US006560541B1

(12) United States Patent
Singh (10) Patent No.: US 6,560,541 B1
(45) Date of Patent: May 6, 2003

(54) PREDICTING RISK OF SERIOUS GASTROINTESTINAL COMPLICATIONS IN PATIENTS TAKING NONSTEROIDAL ANTI-INFLAMMATORY DRUGS

(75) Inventor: Gurkirpal Singh, Woodside, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 09/447,963

(22) Filed: Nov. 23, 1999

Related U.S. Application Data (63) Continuation of application No. 09/296,936, filed on Apr. 22, 1999, now abandoned.
(60) Provisional application No. 60/082,764, filed on Apr. 23, 1998.
(51) Int. Cl.[7] .......................... G01N 33/48; G06F 17/18; G06F 17/60; G06F 17/00
(52) U.S. Cl. .......................... 702/19; 702/179; 705/2; 707/104; 700/90; 700/49; 128/920; 128/923
(58) Field of Search .................... 700/49, 90; 702/179, 702/19; 705/2; 707/104; 128/920, 923

(56) References Cited

PUBLICATIONS

Statistics in Medicine (1989) "A Comparison of Estimated Proportional Hazards Models and Regression Trees" Segal and Bloch, vol. 8, pp. 539–550.*
Gastroenterology (1997) "NSAID–Related Effects on the GI Tract" Singh et al., vol. 112, No. 4, A292.*
Scandanavian Journal of Rheumatology (1996) "Toward an Understanding of NSAID–Related Adverse Events: The Contribution of Longitudinal Data" Fries, J., vol. 25(Suppl 102), pp. 3–8.*

Fries, J., *Nonsteroidal Anti–Inflammatory Drug–Associated Gastropathy: Incidence and Risk Factor Models*, American J. of Medicine, vol. 91, pp. 213–222, Sep. 1991.

Singh, G., *NSAID Induced Gastrointestinal Complications: The ARAMIS Perspective–1997*, The Journal of Rheumatology, pp. 980086–1—980086–9, 1998.

Wolf, P., *Probability of Stroke: A Risk Profile from the Framingham Study*, Stroke, 22(3), pp. 312–318, Mar. 1991.

* cited by examiner

*Primary Examiner*—Marianne P. Allen
*Assistant Examiner*—Lori A. Clow
(74) *Attorney, Agent, or Firm*—Lumen Intellectual Property Services, Inc.

(57) ABSTRACT

A computer-implemented method for calculating estimated risk of serious gastrointestinal (GI) hospitalization of a patient taking nonsteroidal anti-inflammatory drugs includes the steps of obtaining patient values of a plurality of predictive factors, calculating an estimated risk from the patient values, and displaying the estimated risk, preferably on a monitor. The predictive factors may be age, global health status, proportion of time taking prednisone, occurrence of a previous GI side effect, and occurrence of a previous GI hospitalization. Preferably, the estimated risk is calculated from a Cox proportional hazard model, derived from a database of arthritis patients, using either continuous or categorical variables. The continuous model applies a standard Cox model to the predictive factors. The categorical model divides each predictive factor into categories, and assigns a point value to each predictive factor. The point values are added to derive a point total, which is converted to an estimated risk using a predetermined correlation between point total and estimated risk.

3 Claims, 5 Drawing Sheets

GI SCORE

How old are you?

| | |
|---|---|
| under 20 ○ | 55-55 ○ |
| 21-25 ○ | 56-60 ◉ |
| 26-30 ○ | 61-65 ○ |
| 31-35 ○ | 66-70 ○ |
| 36-40 ○ | 71-75 ○ |
| 41-45 ○ | 76-80 ○ |
| 46-50 ○ | 81-85 ○ |
| | over 85 ○ |

How do you rate your current health status on the following scale?

Very Poor ○
Poor ○
Fair ○
Well ◉
Very Well ○

If you are taking prednisone or other corticosteroids, for how many months have you taken them in the past year?

0 ○
1-3 ◉
4-6 ○
7-10 ○
11-12 ○

Have you ever been hospitalized for a stomach or intestinal problem such as a bleeding ulcer or ulcer?

No ○
Yes ◉

If yes, skip the next question.

Have you ever had gastrointestinal side effects (heartburn, stomach pain, nausea, vomiting) when taking NSAID pain relievers?

No ○
Yes ◉

[SUBMIT]

PREDICTING RISK OF SERIOUS GASTROINTESTINAL COMPLICATIONS IN PATIENTS TAKING NONSTEROIDAL ANTI-INFLAMMATORY DRUGS

CROSS-REFERENCE TO RELATED APPLICATIONS

This application is a continuation of copending patent application 09/296,936 filed Apr. 22, 1999, now abandoned, which is based on provisional application 60/082,764 filed Apr. 23, 1998.

STATEMENT REGARDING FEDERALLY SPONSORED RESEARCH OR DEVELOPMENT

This invention was supported in part by grant number AR43584 from the National Institutes of Health (NIH). The U.S. Government has certain rights in the invention.

FIELD OF THE INVENTION

This invention relates generally to methods for predicting risk of medical conditions. More particularly, it relates to methods for predicting risk of serious gastrointestinal complications in patients taking nonsteroidal anti-inflammatory drugs.

BACKGROUND ART

Gastrointestinal (GI) complications related to nonsteroidal anti-inflammatory drug (NSAID) therapy are the most prevalent category of adverse drug reactions in the United States. The most serious and life-threatening complications include ulcers or bleeding, and require immediate hospitalization. The risk of GI hospitalization has been estimated at 1% to 1.5% in people taking NSAIDs, and the risk of death at 0.13%. In 1997, about 16,500 Americans died from bleeding stomach ulcers caused by NSAIDs. Patients with arthritis are among the most frequent users of NSAIDs and are therefore particularly at risk for these side effects. Often, there are no previous symptoms before a patient is hospitalized.

Some patients taking NSAIDs, for example older patients, are believed to be at a much higher risk for GI side effects than others. There is currently no way to accurately determine individual risk, however, even qualitatively. Physicians prescribing NSAIDs to arthritis patients cannot assess the treatment's safety until a side effect occurs. While some risk factors are believed to be important, physicians can currently base drug therapy recommendations only on their intuitive, subjective clinical judgment. In addition, as managed care becomes the health care standard, patients are becoming more informed about their personal health and less trusting of health care providers, and would like to be able to assess their own risk.

Individual risk factors have been suggested in the literature, but it is difficult to estimate an overall patient risk from these various risk factors. Some of the individual risk factors include age, NSAID therapy duration, and use of $H_2$ antagonists, antacids, corticosteroids, or anticoagulants. A multivariate risk factor model for estimation of risk in an individual patient is described in J. F. Fries et al., "Nonsteroidal Anti-Inflammatory Drug-Associated Gastropathy: Incidence and Risk Factor Models," American Journal of Medicine, Vol. 91, pp. 213–222 (1991). The model is a classification tree that provides an estimated risk for each branch of the tree. Different values of predictive factors, for example, age and disease duration, cause branching in one of a number of directions. While it does include a variety of risk factors, the model and its associated GI event score table are cumbersome to use and cannot easily be extended to multiple years. The stepwise logistic regression methods used to develop the model are also not the most accurate for the analysis of longitudinal data, because they are not time oriented. That is, they do not take into account the time to the event or the time of observation for the patients who do not have an event. In addition, the calculation must be done by a health care provider, and is not suited for use by a patient.

There is clearly still a need for a simple and accurate method for determining a patient's risk of a serious GI hospitalization while taking NSAIDs. Once this risk is known, a physician can make appropriate drug therapy recommendations.

OBJECTS AND ADVANTAGES

Accordingly, it is an object of the present invention to provide a simple method for determining the estimated risk of GI hospitalization of a patient taking NSAIDs that:

1) includes many significant variables to calculate an overall risk;
2) is highly accurate;
3) can easily be extended to multiple years;
4) uses data that is easily obtained from a patient;
5) provides a simple additive point system; and
6) can be used by patients without help from a physician.

SUMMARY

These objects and advantages are attained by a computer-implemented method for determining the estimated risk R of serious gastrointestinal hospitalization of a patient taking nonsteroidal anti-inflammatory drugs (NSAIDs). A physician uses the estimated risk R to determine whether an appropriate drug therapy includes NSAIDs.

The method includes three main steps: obtaining patient values of a plurality of predictive factors $x_1, \ldots, x_n$; calculating the estimated risk R from a model applied to the patient values; and displaying the calculated estimated risk R. The predictive factors may include age, baseline global health status, proportion of time taking prednisone, previous occurrence of a GI side effect, and previous occurrence of GI hospitalization.

The model is preferably a Cox proportional hazard model derived from a patient database. In one main embodiment, the estimated risk $R=1-S(1)^B$, where $S(1)$ is a probability of not having a serious GI hospitalization within one year, $B=e^A$, $A=L-M$, $$M = \sum_{i=1}^{n} a_i m_i, \quad L = \sum_{i=1}^{n} a_i x_i,$$

$m_i$ are predetermined mean values of the predictive factors, and $a_i$ are Cox coefficients. Specifically, for n=5 and risk factors listed above, $S(1)=0.99045$, the predetermined mean values are $m_1=56.82$ years, $m_2=41.04$, $m_3=0.374$, $m_4=0.263$, and $m_5=0.013$, and the Cox coefficients are $a_1=0.050$/years, $a_2=0.010$, $a_3=1.109$, $a_4=0.373$, and $a_5=1.957$.

Alternately, the estimated risk can be calculated from a point value method. First, a point value $p_i$ is assigned to each predictive factor, where the point value is related to the patient value of the predictive factor. For example, an age between 61 and 65 receives a point value of 9. The point values may instead be obtained directly from the patient in the first step of the method. Next, the point values for each predictive factor are added to produce a point total P. Finally, the point total P is converted to an estimated risk R. In one embodiment of a Cox point-based categorical method for n=5, the estimated risk $R=1-S(1)^B$, where $S(1)=0.99049$, $B=e^A$, $A=L-M$, $M=2.7662$, and $L=0.237*P$.

DETAILED DESCRIPTION

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

Figure 1:
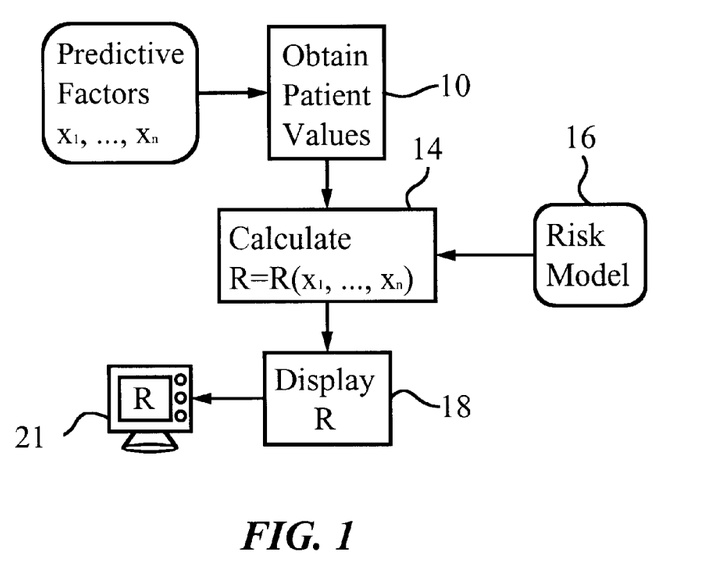
FIG. 1 is a block diagram of the method of the present invention.

The method of the invention is shown in FIG. 1. The invention provides a computer-implemented method for determining an estimated risk R of serious gastrointestinal (GI) hospitalization of a patient taking nonsteroidal anti-inflammatory drugs (NSAIDs). A physician can use the estimated risk, by comparing it with a mean risk, to determine whether or not the patient's drug therapy should include NSAIDs. Because arthritis sufferers are among the most frequent users of NSAIDs, the present method is particularly applicable to arthritis treatment.

For the present invention, a serious GI hospitalization is defined as an inpatient hospitalization of at least 24 hours duration for the following causes: ulcers, GI hemorrhages, perforations, gastritis, abdominal pain, nausea, and vomiting (not due to gastroenteritis). The NSAIDs included are aspirin, diclofenac, etodolac, fenoprofen, flurbiprofen, ibuprofen, indomethacin, ketoprofen, meclofenamate, nabumetone, naproxen, non-acetylated salicylates, oxaprozin, prioxicam, salsalate, sulindac, and tolmetin.

The computer-implemented method works as shown in FIG. 1. In a first step 10, patient values of predictive factors $x_1, \ldots, x_n$ are obtained. Next, in step 14, an estimated risk R is calculated by applying a model 16 to the patient values. Finally, estimated risk R is displayed in step 18, preferably on a computer monitor 21.

The predictive factors may be any factors known to affect patient risk of a serious GI hospitalization. Preferably, the predictive factors are quantities that are easily obtained from a patient through a series of simple questions, and are not quantities obtained only through a physical examination. A preferred embodiment of the method uses five predictive factors: $x_1$=age, $x_2$=baseline global health status (hereafter referred to as "global"), $x_3$=proportion of time taking prednisone ("prednisone"), $x_4$=previous occurrence of a GI side effect of NSAID therapy ("side effect"), and $x_5$=previous occurrence of GI hospitalization ("hospitalization"). The predictive factors do not necessarily have quantitative values. Previous occurrence predictive factors may have values of "yes" or "no," and global health status may have values of "very well" or "poor." Variable types with a limited number of predefined qualitative values can be defined in most computer languages.

The predictive factors have precise definitions. Predictive factor $x_1$ is the patient's current age.

Baseline global health status is an assessment of a patient's overall condition, as it affects his or her arthritis. Patients give a value for $x_2$ based on how they feel, using a scale from 0 to 100, in which 0 is very well and 100 is very poor.

Prednisone is an oral corticosteroid often prescribed in conjunction with NSAIDs to rheumatoid arthritis patients. Predictive factor $x_3$ measures the percent of time within the last year the patient took prednisone during NSAID therapy.

GI side effects of NSAID therapy include abdominal pain, heartburn, and dyspepsia. For patients with one or more hospitalizations, predictive factor $x_4$ indicates whether the patient had a GI side effect to NSAID therapy before the hospitalization, or whether the patient had a prior GI hospitalization. For patients without prior hospitalizations, $x_4$ indicates presence of a side effect at any time during NSAID therapy. If yes, $x_4=1$; if no, $x_4=0$.

Finally, GI hospitalization includes prior hospitalization for the reasons listed above when the patient was and was not taking NSAIDs. If yes, $x_5=1$; if no, $x_5=0$. Patients with previous GI hospitalizations are automatically considered to have had a prior GI side effect; that is, if $x_5=1$, then $x_4=1$.

Risk model 16 is preferably a multivariate Cox proportional hazard model. Derivation of the model is described below. Cox models are well known in the art and are described in most standard statistical textbooks. A Cox model can be used to predict risk in any number of years in the future. Preferably, the current invention predicts risk within the next year. There are two embodiments of the Cox model, a continuous model and a point-based categorical model. The continuous model uses the basic Cox equations below, and the categorical model uses a modified version of the same equations. After model 16 is established, estimated risk R is calculated as follows in step 14 for the continuous model using the five predictive factors $x_1, \ldots, x_5$.

$R=1-S(1)^B$, where:

S(1) is mean one-year survival probability, i.e. (1−S(1)) is mean one-year risk, $B=e^A$, $A=L-M$, $$L = \sum_{i=1}^{n} a_i x_i$$

= Cox equation evaluated at patient values of predictive factors, $$M = \sum_{i=1}^{n} a_i m_i$$

= Cox equation evaluated at mean values of predictive factors, and $a_i$ are Cox coefficients.

Using the five predictive factors $x_1, \ldots, x_5$, the specific values are: n=5, S(1)=0.99045, $m_1$=56.82 years, $m_2$=41.04, $m_3$=0.374, $m_4$=0.263, $m_5$=0.013, $a_1$=0.050/years, $a_2$=0.010, $a_3$=1.109, $a_4$=0.373, and $a_5$=1.957. For these values, M=3.7633 and (1−S(1))=0.00955=0.96%.

For example, consider two patients with the following characteristics:

Patient 1

Age=34 Global=20 Prednisone=0.17 Side Effect=No Hospitalization=No

M=3.7633

L=[(0.050*34)+(0.010*20)+(1.109*0.17)+(0.373*0)+(1.957*0)]=2.069069

A=L−M=−1.6932

$B=e^A=e^{-1.6932}=0.1839$ $S(1)^B=0.99045^{0.1839}=0.9982$ $R=1-S(1)^B=1-0.9982=0.00176$

Patient 1 has a risk of 0.18%, which is well below the mean risk of 0.96%. Patient 1 is an excellent candidate for NSAID therapy.

Patient 2

Age=64 Global=60 Prednisone=0.8 Side Effect=Yes Hospitalization=No

M=3.7633

L=[(0.050*67)+(0.010*60)+(1.109*0.8)+(0.373*1)+(1.957*0)]=5.0598

A=L−M=1.2975

$B=e^A=e^{1.2975}=3.6601$ $S(1)^B=0.99045^{3.6601}=0.9655$ $R=1-S(1)^B=1-0.9655=0.0345$

Patient 2 has a risk of 3.5%, which is well above the mean risk of 0.96%. Patient 2's physician would probably not prescribe or recommend an NSAID.

It is obvious to one skilled in computer programming how to program a computer to calculate estimated risk R from the above equations. Any suitable programming language may be used.

Figure 2:
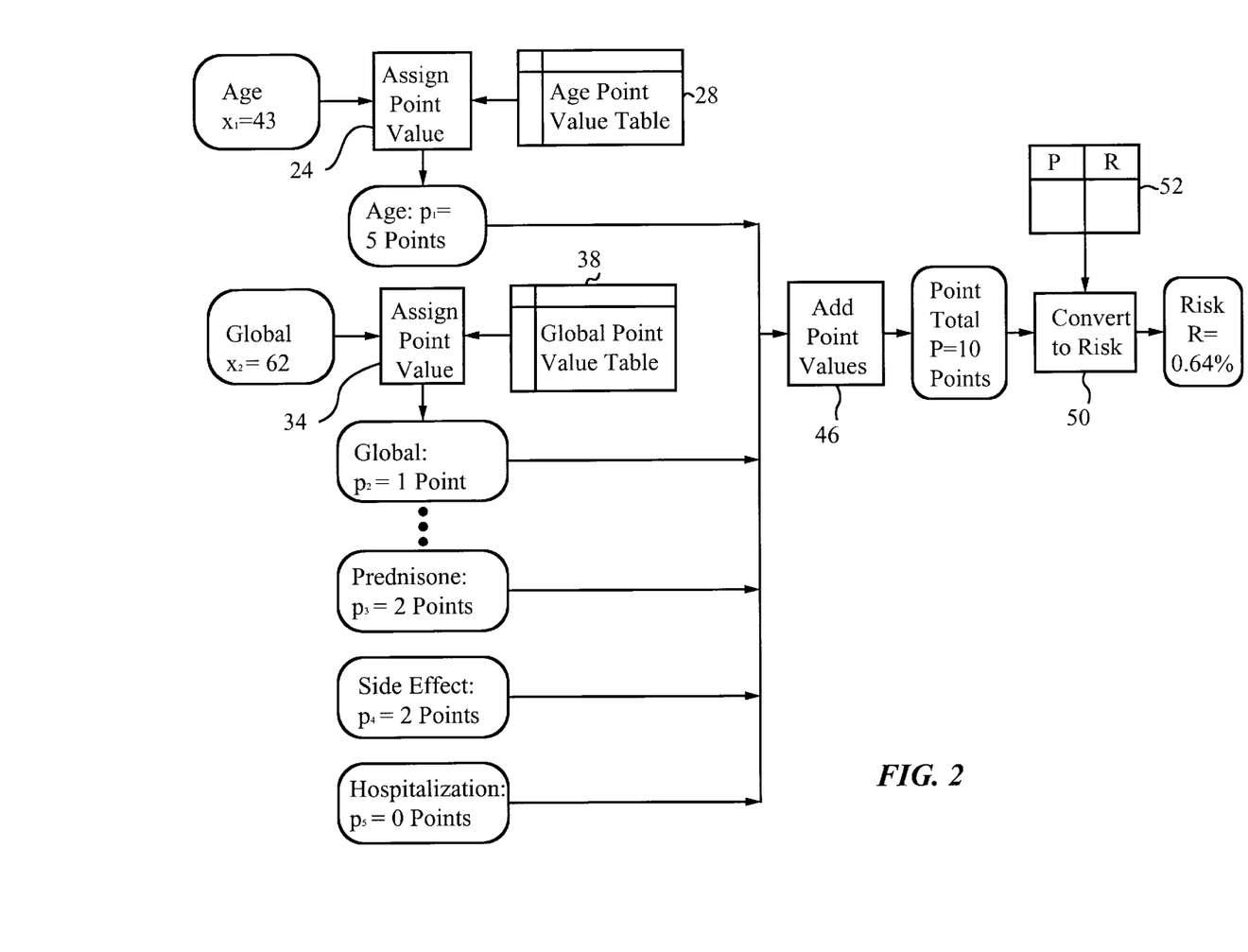
FIG. 2 is a block diagram of a point-based embodiment of the method.

FIG. 2 is a block diagram showing the estimated risk calculation step of a second embodiment of the model, the point-based categorical model. FIG. 2 shows an example of the method applied to a particular patient. Rather than using continuous predictive factors as described above, this embodiment divides each predictive factor into discrete categories, with each category including a range of values. Point values are then assigned to each category. Patient values are obtained either as specific values, or as categories. For example, a patient's age might be 62, which corresponds to an age range of 61–65. Alternately, a patient will only be able to enter a range value for his or her age.

Preferably, the categorical model uses the same five predictive factors $x_1, \ldots, x_5$ as the continuous model uses. Definitions may be modified to better suit division into categories. For example, $x_2$, global health status, may be rated on a categorical scale from very well to very poor. It may also be rated on a scale from 0 to 100, but reversed from the scale of the continuous model. For the categorical model, a higher value corresponds to better health status. Rather than percent of time, $x_3$ may be the number of months in the last year during the which the patient took prednisone. The following description is for the predictive factors $x_1, \ldots, x_5$, but a model using any desired predictive factors is within the scope of the present invention.

For each of the predictive factors $x_1, \ldots, x_5$, point values $p_1, \ldots, p_5$ will be assigned. In the example shown in FIG. 2, $x_1=43$. In a first step 24, a point value $p_1$ is assigned to predictive factor $x_1$ using age point value table 28, shown in Table 1. As determined from Table 1, for $x_1=43$, $p_1=5$.

This process is repeated for every predictive factor. As shown in FIG. 2, baseline global health status predictive factor $x_2=62$. In step 34, a point value $p_2$ is assigned using global point value table 38. Point values $p_3$, $p_4$, and $p_5$ are assigned similarly. The remaining point value tables are found in Tables 2–5. The point value tables may be altered as necessary as the predictive factor definitions are changed.

In an alternate embodiment of the point-based method, point values $p_1, \ldots, p_5$ are obtained directly from the patient, without first obtaining patient values of predictive factors $x_1, \ldots, x_5$. Patients may be given the necessary tables, from which they can determine the appropriate point values.

Referring again to FIG. 2, point values $p_1, p_2, p_3, p_4$, and $p_5$ are added in step 46 to obtain a point total P (in this example, 10 points), which is then converted in step 50 to estimated risk R (0.640%).

Conversion step 50 uses a correlation 52 between point total P and risk R. There are two main embodiments of point total-risk correlation 52. Estimated risk R can be calculated from the categorical Cox model equations, which are as follows for n=5:

$R=1-S(1)^B$,

S(1)=0.99049, 1−S(1)=0.00951, i.e., mean one-year risk is 0.951%, $B=e^A$,

A=L−M,

M=2.7662 categorical Cox equation evaluated at mean point values,

L=0.237*P=categorical Cox equation evaluated at patient point values.

Estimated risk R can also be calculated from a point total-risk table, Table 6. Table 6 is calculated using the equations above and stored in the computer.

Estimated risk R can be displayed as either quantitative or qualitative probability of serious GI hospitalization within the next year. Instead of the numerical estimated risks calculated from the equations above, point total P can be converted directly to a qualitative risk. Qualitative risk can have four categories: below average risk, for a point total between 0 and 5; moderate risk, for a point total between 6 and 12; moderately high risk, for a point total between 13 and 17; and high risk, for a point total of 18 or above. Qualitative risk can also be expressed as a relative increase over background risk when not taking NSAIDs. Mean risk point total, determined by applying the calculation algorithm to mean values of each predictive factor, is between 11 and 12, at the high end of moderate risk. Point total-risk correlation 52 then lists point totals and corresponding qualitative estimated risk.

Alternately, estimated risk R may first be calculated as a quantitative risk and then converted to a qualitative risk. This can be done for both the continuous and the categorical model.

The computer-implemented method can be used by a patient, physician, or other party. Depending on the estimated risk value, the patient seeks advice from the physician. Based on the result, the physician might decide to select a different NSAID, adjust the NSAID dose, limit the duration of NSAID use, substitute alternative pain-relief medications, for example, COX-2 inhibitors, or prescribe medications to help protect the GI system during NSAID use.

Figure 3A:
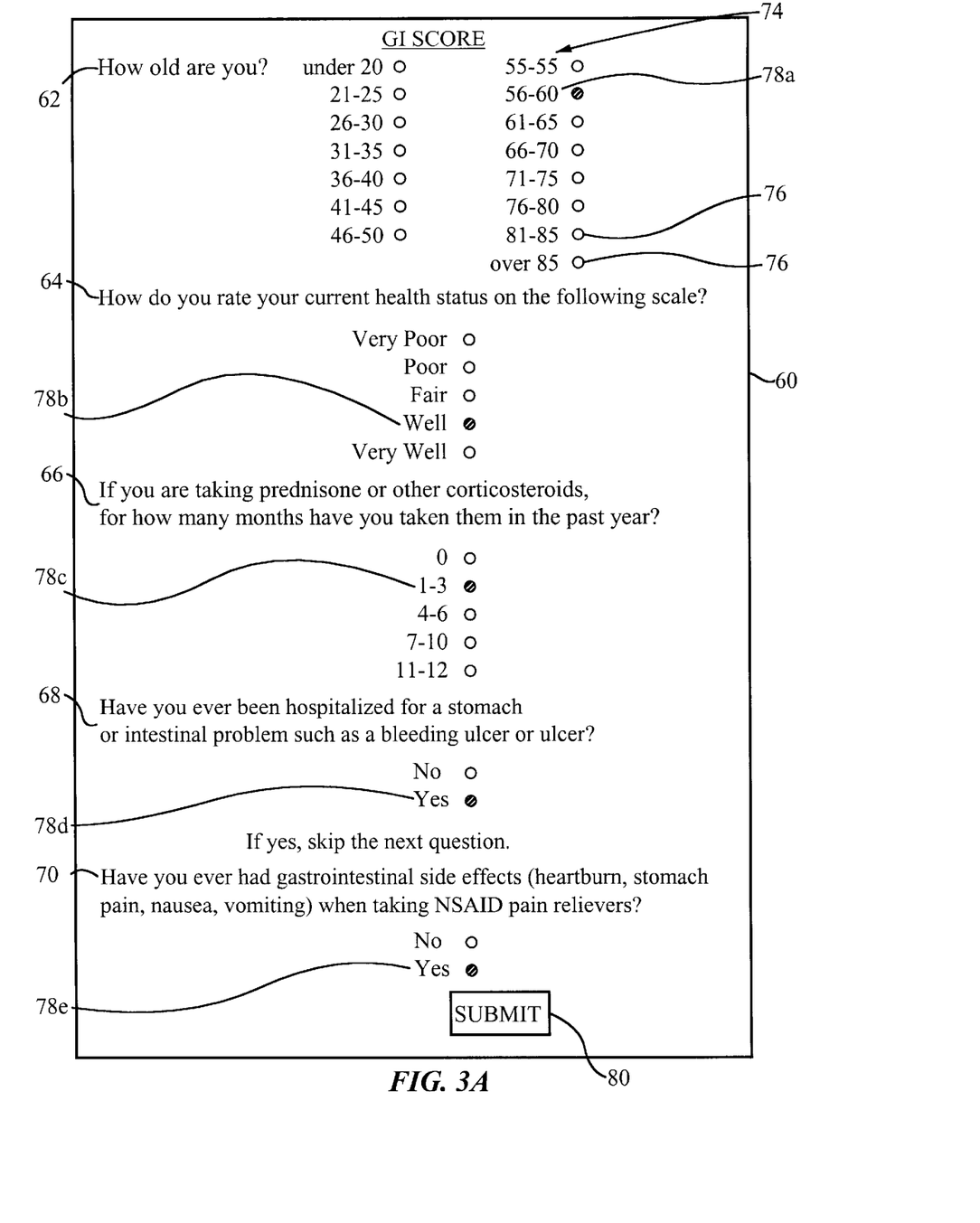
FIG. 3A is a diagram of a graphical user interface for obtaining patient values.

FIG. 3A shows a graphical user interface of a GI SCORE (Stanford Calculator of Risk for Events) for obtaining patient values of predictive factors. A Web page 60 contains a list of questions 62, 64, 66, 68, and 70, used to obtain the patient values. After each question is a list of possible patient values 74 and radio buttons 76. A user selects the appropriate radio buttons indicating his or her patient values 78 and submits the values by clicking a submit button 80.

Figure 3B:
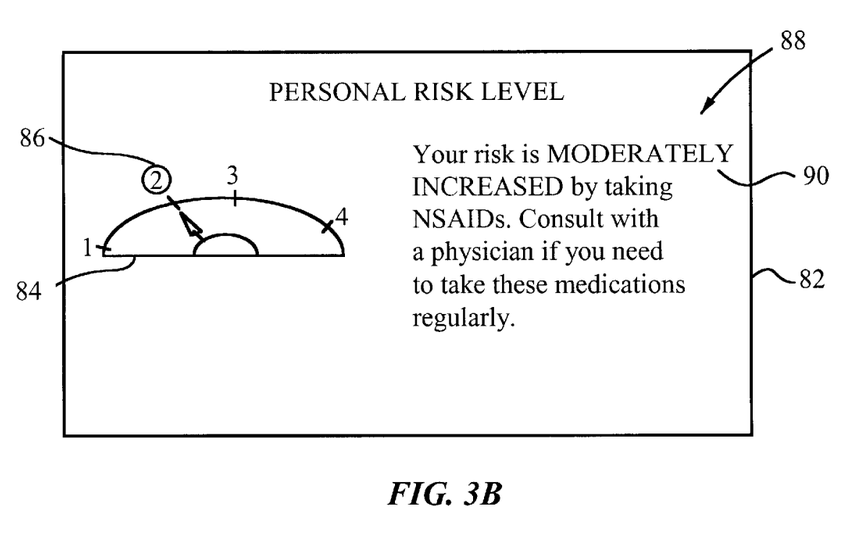
FIG. 3B is a diagram of a graphical user interface for displaying estimated risk.

After page 60 is submitted, the Web server calculates the estimated risk and sends the result to the client. FIG. 3B shows a corresponding Web page 82 used to display the estimated risk, which is a qualitative estimated risk. Page 82 includes an indicator dial 84 pointing to patient estimated risk level 86, in this case 2, which corresponds to a moderate risk. Paragraph 88 includes a risk level label 90, for example, MODERATELY INCREASED. Paragraph 88 may also contain a recommendation for consulting with a medical professional. A user can then print pages 60 and 82 and bring the printed pages to a physician consultation.

Both the continuous and categorical models were developed using prospectively collected, longitudinal data from the Arthritis, Rheumatism, and Aging Medical Information System (ARAMIS). The database has a total sample of 3,883 rheumatoid arthritis patients from 8 ARAMIS centers in the United States and Canada. The patients were followed for a total of 19,691 patient years during which they were taking NSAIDs for a total of 15,638 years. Medication and hospitalization data were collected semi-annually by patient self-report using a Health Assessment Questionnaire along with data on demographics, functional status, side effects, health behaviors, etc. All hospitalizations were audited by requesting discharge summaries to confirm the dates, diagnoses, procedures, and other information. For development of the present invention, hospitalization data were from 303 patients with 417 serious GI hospitalizations. Data for non-hospitalized patients were also used. For each eligible patient, baseline covariates were determined. These covariates include gender, age, education level, disease duration, disability level, pain scale, smoking, and the five predictive factors listed above.

Univariate Cox proportional hazard models were constructed using each covariate as a predictor. The occurrence of a GI hospitalization was the dependent variable, and time on NSAIDs was the censoring variable. In part based on these results, a subset of variables were tested in a series of stepwise multivariate Cox proportional hazard models. Finally, a set of appropriate predictive factors for a multivariate model were chosen.

The continuous model was developed using standard statistical techniques. The point-based categorical model was derived from a modified Cox model. Each predictive factor was divided into categories, equivalent to the predictive factor ranges listed above in the point value tables. Each category was assigned a value; for example, an age between 25 and 30 has a categorical value of 2. Cox coefficients were then derived using the categorical variables, and the category values were adjusted until all of the derived coefficients were approximately integer multiples of the same value, 0.2. For each predictive factor, the integer multiple was then distributed across the point values for the categories. For example, a coefficient of 1.24 corresponds to an integer multiple of 6, and therefore 6 points to be distributed over the number of categories. If there were three categories, the lowest risk category would receive 0 points, the next (middle) would receive 3 points, and the highest category would receive 6 points. This explains why, for example, point values for the prior hospitalization predictive factor are either 0 or 8. After the category adjustments, the actual coefficients were averaged to derive a mean coefficient of 0.237. Because each predictive factor has the same coefficient, the Cox equation is simplified. The estimated risk is then calculated as above: $R=1-S(1)^B$, $B=e^A$, $A=L-M$, M is the categorical Cox equation evaluated at mean point values, and L is the mean coefficient multiplied by the total number of points. The estimated risk R evaluates to a constant corresponding to each particular number of points. If the coefficients were different, each point value would be multiplied by its own coefficient to calculate L, and the model would lose its simplicity and appeal.

Figure 4:
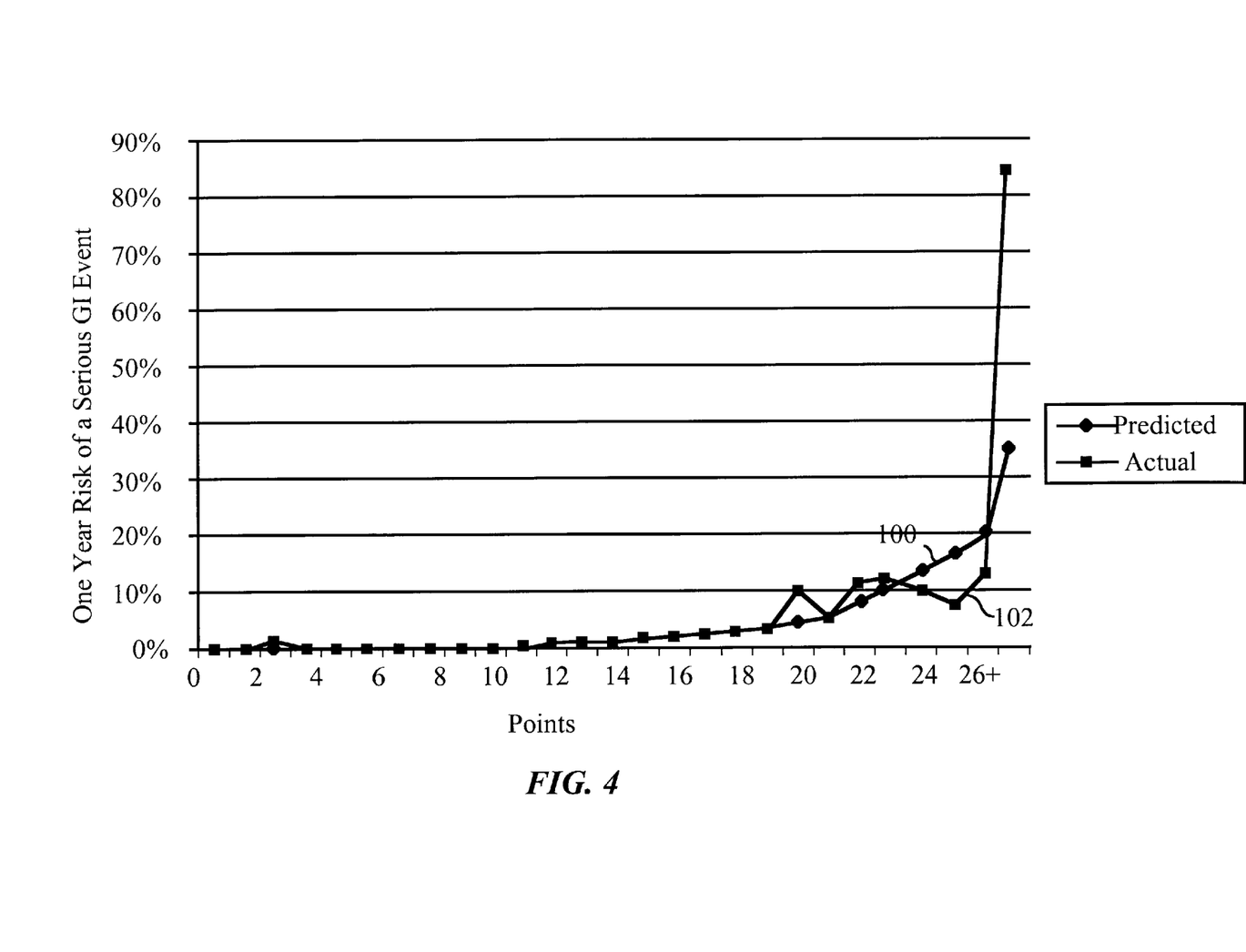
FIG. 4 is a plot of estimated risk versus point value for actual patients and as determined by the method of FIG. 2.

FIG. 4 is a plot of one year risk of a serious GI event versus point total, for the model prediction, curve 100, and for the actual results from the ARAMIS data, curve 102. Actual results 102 were found by calculating the number of points for each eligible patient in the database according to the above scheme, and then determining the percentage of patients with a given point total who suffered a serious GI event within a year of recording the predictive factors. FIG. 4 show the extremely high accuracy of the point-based categorical method. Divergence of curves 100 and 102 at higher point totals occurs mainly because of the small number of patients in the database with those high point totals. In order for the method of the present invention to be widely implemented, it must be both simple to use and highly accurate. It was designed to be simple, and FIG. 4 clearly shows that it can be trusted for accurate risk predictions.

It will be clear to one skilled in the art that the above embodiments may be altered in many ways without departing from the scope of the invention. For example, predictive factors may be added or removed, and the exact point values for each category will need to be modified as the number and type of predictive factors change. Accordingly, the scope of the invention should be determined by the following claims and their legal equivalents.

TABLE 1

| Age | Point Value | Age | Point Value | Age | Point Value |
|---|---|---|---|---|---|
| 20 or less | 0 | 41–45 | 5 | 66–70 | 10 |
| 21–25 | 1 | 46–50 | 6 | 71–75 | 11 |
| 26–30 | 2 | 51–55 | 7 | 76–80 | 12 |
| 31–35 | 3 | 56–60 | 8 | 81–85 | 13 |
| 36–40 | 4 | 61–65 | 9 | Over 85 | 14 |

TABLE 2

| Global Health Status | Point Value |
|---|---|
| 0–10 | Very poor | 4 |
| 11–35 | Poor | 3 |
| 36–50 | Fair | 2 |
| 51–90 | Well | 1 |
| 91–100 | Very Well | 0 |

TABLE 3

| Prednisone | Point Value |
|---|---|
| 0 months | 0 |
| 1–3 months | 1 |
| 4–6 months | 2 |
| 7–10 months | 3 |
| 11–12 months | 4 |

TABLE 4

| GI Side Effect | Point Value |
|---|---|
| No | 0 |
| Yes | 2 |

TABLE 5

| GI Hospitalization | Point Value |
|---|---|
| No | 0 |
| Yes | 8 |

TABLE 6

| Point Total | 0 | 1 | 2 | 3 | 4 | 5 | Below Average Risk |
|---|---|---|---|---|---|---|---|
| Risk/% | 0.060 | 0.076 | 0.096 | 0.122 | 0.155 | 0.196 | |
| Point Total | 6 | 7 | 8 | 9 | 10 | 11 | 12 | Moderate |
| Risk/% | 0.249 | 0.315 | 0.399 | 0.506 | 0.640 | 0.811 | 1.027 | Risk |
| Point Total | 13 | 14 | 15 | 16 | 17 | Moderately High Risk | | |
| Risk/% | 1.299 | 1.644 | 2.079 | 2.627 | 3.318 | | | |
| Point Total | 18 | 19 | 20 | 21 | 22 | 23 | 24 | High Risk |
| Risk/% | 4.187 | 5.277 | 6.64 | 8.34 | 10.45 | 13.055 | 16.247 | |

What is claimed is:

1. A computer-implemented method for determining an estimated risk R of serious gastrointestinal (GI) hospitalization of a patient taking non-steroidal anti-inflammatory drugs, said method comprising the steps of:
  a) obtaining patient values of predictive factors $x_1, \ldots, x_5$ wherein said predictive factors are age, baseline global health status, proportion of time taking prednisone, previous occurrence of a GI side effect and previous occurrence of GI hospitalization;
  b) calculating said estimated risk R from a model applied to said patient values, wherein said model is a Cox proportional hazard model that is based on longitudinal data, wherein said estimated risk R is calculated according to $R=1-S(1)^B$, wherein:
   S(1) is a mean probability of not having a serious GI hospitalization within one year, and
   $B=e^A$, $A=L-M$, $$M = \sum_{i=1}^{5} a_i m_i, \text{ and } L = \sum_{i=1}^{5} a_i x_i,$$

wherein $m_i$ are a plurality of predetermined mean values of said predictive factors, and $a_i$ are a plurality of Cox coefficients, wherein S(1) is 0.99045, wherein said plurality of predetermined mean values are $m_1$ is 56.82 years, $m_2$ is 41.04, $m_3$ is 0.374, $m_4$ is 0.263, and $m_5$ is 0.013, and wherein said plurality of Cox coefficients are $a_1$ is 0.050/years, $a_2$ is 0.010, $a_3$ is 1.109, $a_4$ is 0.373, and $a_5$ is 1.957; and
  c) displaying said estimated risk R on a display wherein said estimated risk R is displayed as a quantitative or qualitative measure.

2. A computer-implemented method for determining an estimated risk R of serious gastrointestinal (GI) hospitalization of a patient taking non-steroidal anti-inflammatory drugs, said method comprising the steps of:
  a) obtaining patient values of predictive factors $x_1, \ldots, x_5$ wherein said predictive factors are age, baseline global health status, proportion of time taking prednisone, previous occurrence of a GI side effect and previous occurrence of GI hospitalization;
  b) calculating said estimated risk R from a model applied to said patient values, wherein said model is a Cox proportional hazard model that is based on longitudinal data wherein said step of calculating said estimated risk R comprises the step of:
   i) assigning a point value to each of said predictive factors, wherein said point value is related to said patient value of said predictive factor;
   ii) adding said point values for each of said predictive factors to obtain a point total P; and
   iii) converting said point total P to said estimated risk R, wherein said step of converting uses a correlation between said point values and said estimated risk R or a point total P—risk table, wherein said $R=1-S(1)^B$, wherein S(1) is 0.99049, $B=e^A$, $A=L-M$, M is 2.7662, and L equals 0.237*P; and
  c) displaying said estimated risk R on a display wherein said estimated risk R is displayed as a quantitative or qualitative measure.

3. A computer-implemented method for determining an estimated risk R of serious gastrointestinal (GI) hospitalization of a patient taking non-steroidal anti-inflammatory drugs, said method comprising the steps of:
  a) obtaining patient values of predictive factors $x_1, \ldots, x_5$ wherein said predictive factors are age, baseline global health status, proportion of time taking prednisone, previous occurrence of a GI side effect and previous occurrence of GI hospitalization, wherein said predictive factors are point values $p_1, \ldots, p_5$ from said patient of said predictive factors $x_1, \ldots, x_5$, wherein:
   $p_1$ is:
    0 when said age is below 20,
    1 when said age is between 21 and 25,
    2 when said age is between 26 and 30,
    3 when said age is between 31 and 35,
    4 when said age is between 36 and 40,
    5 when said age is between 41 and 45,
    6 when said age is between 46 and 50,
    7 when said age is between 51 and 55,
    8 when said age is between 56 and 60,
    9 when said age is between 61 and 65,
    10 when said age is between 66 and 70,
    11 when said age is between 71 and 75,
    12 when said age is between 76 and 80,
    13 when said age is between 81 and 85, and
    14 when said age is above 85;
   $p_2$ is:
    0 when said baseline global health status is between 91 and 100,
    1 when said baseline global health status is between 51 and 90,
    2 when said baseline global health status is between 36 and 50,
    3 when said baseline global health status is between 11 and 35, and 4 when said baseline global health status is between 0 and 10;

$p_3$ is:
- 0 when said number of months taking prednisone is 0,
  - 1 when said number of months taking prednisone is between 1 and 3,
  - 2 when said number of months taking prednisone is between 4 and 6,
  - 3 when said number of months taking prednisone is between 7 and 10, and
- 4 when said number of months taking prednisone is between 11 and 12;

$p_4$ is:
- 0 when said patient potential previous occurrence of a GI side effect is no, and
- 2 when said potential previous occurrence of a GI side effect is yes; and $p_5$ is:
- 0 when said potential previous occurrence of GI hospitalization is no, and
- 8 when said potential previous occurrence of GI hospitalization is yes;

b) calculating said estimated risk R from a model applied to said patient values, wherein said model is a Cox proportional hazard model that is based on longitudinal data; and c) displaying said estimated risk R on a display wherein said estimated risk R is displayed as a quantitative or qualitative measure.

* * * * *